(12) United States Patent
Fodness-Bondhus

(10) Patent No.: US 12,708,776 B2
(45) Date of Patent: Aug. 18, 2026

(54) PACING TOOL

(71) Applicant: BOSTON SCIENTIFIC SCIMED, INC., Maple Grove, MN (US)

(72) Inventor: Spencer Fodness-Bondhus, Columbia Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 218 days.

(21) Appl. No.: 18/598,295

(22) Filed: Mar. 7, 2024

(65) Prior Publication Data

US 2024/0307694 A1 Sep. 19, 2024

Related U.S. Application Data

(60) Provisional application No. 63/452,548, filed on Mar. 16, 2023.

(51) Int. Cl.

| | |
|---|---|
| ***A61N 1/362*** | (2006.01) |
| ***A61M 25/09*** | (2006.01) |
| ***A61N 1/05*** | (2006.01) |

(52) U.S. Cl.

CPC ............. *A61N 1/362* (2013.01); *A61N 1/056* (2013.01); *A61M 25/09* (2013.01)

(58) Field of Classification Search

CPC . G01R 31/54; G01R 1/06705; G01R 1/06794

See application file for complete search history.

(56) References Cited

U.S. PATENT DOCUMENTS

| | | | | |
|---|---|---|---|---|
| 4,857,857 A * | 8/1989 | Valenti | G01R 31/52 | 324/555 |
| 5,238,004 A | 8/1993 | Sahatjian et al. | | |
| 5,413,508 A | 5/1995 | Obara | | |
| 5,552,713 A * | 9/1996 | Rashidi | A61B 5/283 | 324/555 |
| 6,508,803 B1 | 1/2003 | Horikawa et al. | | |
| 9,179,857 B2 | 11/2015 | Lee et al. | | |
| 10,173,052 B2 | 1/2019 | Daniels | | |
| 11,420,046 B2 | 8/2022 | Daniels et al. | | |
| 2002/0045927 A1 | 4/2002 | Moore et al. | | |

FOREIGN PATENT DOCUMENTS

| | | |
|---|---|---|
| EP | 2480282 B1 | 8/2015 |

* cited by examiner

*Primary Examiner* — Paula J Stice

(74) *Attorney, Agent, or Firm* — Seager, Tufte & Wickhem LLP

(57) ABSTRACT

A pacing tool adapted for use with a guidewire to allow the guidewire to be used for pacing includes a body defining an elongate cavity adapted to receive a guidewire. A compressible electrical contact is disposed at a proximal end of the elongate cavity and is adapted to shorten axially when a proximal end of the guidewire makes contact with the compressible electrical contact. An electrical cable is electrically coupled with the compressible electrical contact and is adapted to be electrically coupled with a pacing system. The pacing tool may include a guidewire holder for releasably securing the guidewire within the elongate cavity.

20 Claims, 13 Drawing Sheets

10
14
16
18
20
22
24
26
28
30
32
34
36
38
40
42
44
50
52
54

36
42
20
38
34
44
52
40
22
32
30
28
24
26
16
50
14
10
18
54

250

260
264
266

252
6
6
250
254

262
8
8
260

Pacing System
450
452
440
420
454
424
426
422
423
414
412
416
320
310
330
300
446
438
442
444
410

PACING TOOL

CROSS REFERENCE TO RELATED APPLICATIONS

This application claims the benefit of priority of U.S. Provisional Application No. 63/452,548 filed Mar. 16, 2023, the entire disclosure of which is hereby incorporated by reference.

TECHNICAL FIELD

The disclosure relates generally to pacing tools for use in forming an electrical connection with a guidewire in order to pace with the guidewire.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example may be found in a pacing tool adapted for use with a guidewire to allow the guidewire to be used for pacing, the guidewire having an electrically conductive proximal end. The pacing tool includes a body defining an elongate cavity adapted to receive a guidewire, the elongate cavity including a proximal end. A compressible electrical contact is disposed at the proximal end of the elongate cavity, the compressible electrical contact adapted to shorten axially when a proximal end of the guidewire makes contact with the compressible electrical contact. A cable is electrically coupled with the compressible electrical contact, the cable adapted to be electrically coupled with a pacing system.

Alternatively or additionally, the body may include an electrically insulative material.

Alternatively or additionally, the elongate cavity may have an inner diameter that is adapted to frictionally engage an outer surface of the guidewire, thereby holding the guidewire in place within the elongate cavity with the proximal end of the guidewire electrically coupled with the compressible electrical contact.

Alternatively or additionally, the elongate cavity may have an inner diameter that is greater than an outer diameter of the guidewire, and wherein the pacing tool may further include an actuatable element that is adapted to releasably engage a side of the guidewire when the guidewire is present within the elongate cavity in order to hold the guidewire in place within the elongate cavity.

Alternatively or additionally, the actuatable element may include a gripper adapted to releasably engage the side of the guidewire.

Alternatively or additionally, the actuatable element may further include a push button that is connected to the gripper via a compressible member.

Alternatively or additionally, the compressible member may include a spring.

Alternatively or additionally, the compressible electrical contact may include a pogo pin.

Alternatively or additionally, the compressible electrical contact may include a barrel element adapted to be secured to the proximal end of the elongate cavity, a plunger element slidingly disposed within the barrel element and extending distally from the barrel element, and a spring disposed between the barrel element and the plunger element, the spring adapted to bias the plunger element distally relative to the barrel element but to allow the plunger element to move proximally relative to the barrel element in response to the guidewire being pushed against the compressible electrical contact.

Alternatively or additionally, the plunger element may be adapted to be held captive relative to the barrel element.

Alternatively or additionally, the barrel element may be adapted to be electrically coupled with the electrical cable.

Another example may be found in a pacing tool adapted for use with a guidewire to allow the guidewire to be used for pacing, the guidewire having an electrically conductive proximal end. The pacing tool includes a tool body defining an elongate cavity extending within the body, the elongate cavity adapted to accommodate a guidewire extending therein, and a channel orthogonal to the elongate cavity and coupled with the elongate cavity. A guidewire holder is slidingly disposed within the channel, the guidewire holder adapted to releasably engage a side of the guidewire when the guidewire is present within the elongate cavity in order to hold the guidewire in place within the elongate cavity. A spring-loaded pin is disposed at the proximal end of the elongate cavity, the spring-loaded pin adapted to shorten axially when a proximal end of the guidewire makes contact with the spring-loaded pin.

Alternatively or additionally, the pacing tool may further include a cable electrically coupled with the spring-loaded pin, the cable adapted to be electrically coupled with a pacing system.

Alternatively or additionally, the spring-loaded pin may include a barrel element adapted to be secured to the proximal end of the elongate cavity, a plunger element slidingly disposed within the barrel element and extending distally from the barrel element, and a spring disposed between the barrel element and the plunger element, the spring adapted to bias the plunger element distally relative to the barrel element but to allow the plunger element to move proximally relative to the barrel element in response to the guidewire being pushed against the spring-loaded pin.

Alternatively or additionally, the plunger element may be adapted to be held captive relative to the barrel element.

Alternatively or additionally, the tool body may include an electrically insulative material.

Alternatively or additionally, the elongate cavity may have a diameter that is greater than a diameter of the guidewire such that the guidewire is adapted to slide into the elongate cavity and is releasably held in place via the guidewire holder.

Another example may be found in a pacing tool adapted for use with a guidewire to allow the guidewire to be used for pacing, the guidewire having an electrically conductive proximal end. The pacing tool includes a tool body defining an elongate cavity extending within the body, the elongate cavity adapted to accommodate a guidewire extending therein, and a channel orthogonal to the elongate cavity and coupled with the elongate cavity. A guidewire holder is slidingly disposed within the channel. The guidewire holder includes a gripper adapted to releasably engage a guidewire disposed within the elongate cavity, a plunger adapted to be pushed in order to releasably engage the gripper, and a spring disposed between the gripper and the plunger. A spring-loaded pin is disposed at a terminal end of the elongate cavity. A cable is electrically coupled with the spring-loaded pin, the cable adapted to be electrically coupled with a pacing system.

Alternatively or additionally, the spring-loaded pin may include a barrel element adapted to be secured to the terminal end of the elongate cavity, a plunger element slidingly disposed within the barrel element and extending distally from the barrel element, and a spring disposed between the barrel element and the plunger element, the spring adapted to bias the plunger element distally relative to the barrel element but to allow the plunger element to move proximally relative to the barrel element in response to the guidewire being pushed against the spring-loaded pin.

Alternatively or additionally, the guidewire holder may be adapted to translate within the channel.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
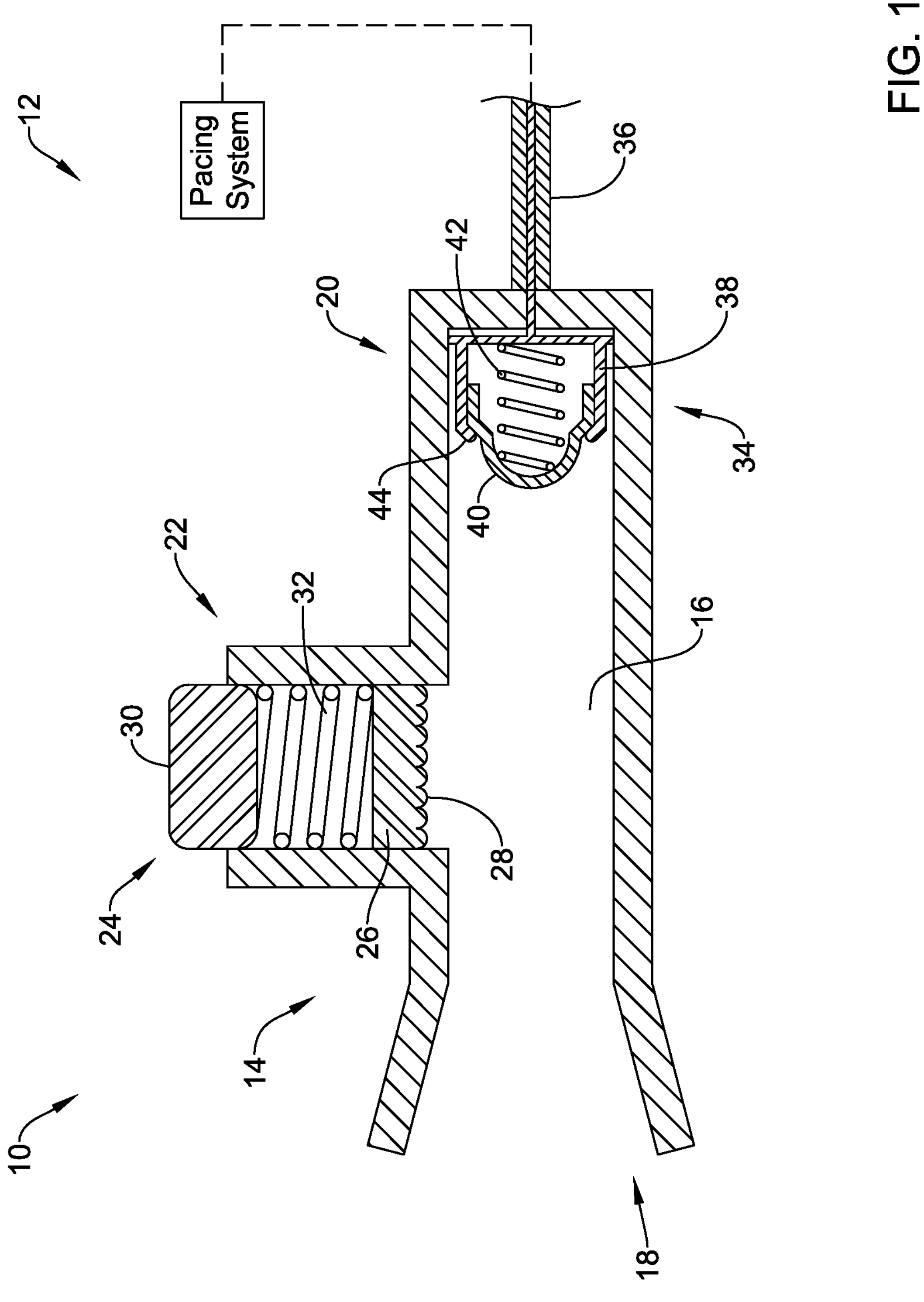
FIG. 1 is a schematic view of an illustrative pacing tool.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the present disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the present disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Guidewires are used in a large number of medical procedures. Guidewires may be advanced through a patient's vasculature in order to gain access to a desired treatment site within the vasculature. Once the desired treatment site has been reached, the guidewire may be used to deliver a variety of different medical devices through the vasculature to the desired treatment site for use in a number of different procedures. In some instances, the vasculature includes tortuous portions that require use of a highly flexible guidewire. In some instances, a high degree of torque transmission may be useful in a guidewire. In some instances, a high degree of pushability may be useful in a guidewire. Accordingly, a large number of different guidewires have been developed, for a variety of different uses in a myriad of different medical procedures.

In some cases, a guidewire may be used in a procedure in which the physician or other professional wants to deliver electrical pacing to tissue within the body using the guidewire. In some cases, the physician or other professional may be using a guidewire to deliver an implant for implantation within the heart. Some replacement cardiac valves may be delivered over a guidewire, for example. In some instances, the physician or other professional may want to utilize the guidewire for delivering pacing pulses to the cardiac tissue. In some instances, for example, temporarily rapidly pacing the heart can be beneficial in implanting some replacement cardiac valves. Being able to pace with the guidewire that is already in position may mean that one less medical device needs to be used.

It will be appreciated that using a guidewire that was likely designed with other design characteristics in mind may not be optimal for pacing. One example of this is being able to connect a pacing system to the proximal end of the guidewire because the guidewire may not be designed to facilitate connecting a lead or cable from a pacing system to the proximal end of the guidewire. Although guidewires can have any of a variety of different designs and constructions, in some instances a guidewire may have a proximal end that is both electrically conductive and exposed. In some instances, using a pacing tool may provide an improved electrical connection between a pacing system and a guidewire.

FIG. 1 is a schematic view of an illustrative pacing tool 10 that may be used to form a temporary electrical connection between a guidewire (not shown in FIG. 1) and a pacing system 12. The pacing system 12 is shown schematically, and may include additional components that are not shown. The pacing system 12 may include a controller that determines when and how to pace, for example. The pacing tool 10 is adapted to releasably receive a proximal region of a guidewire and to make electrical contact with the proximal region of the guidewire. In some cases, the pacing tool 10 may be adapted to provide an electrical connection with a proximal end of the guidewire. While many guidewires include insulative coatings over various portions of the guidewire, some guidewires have a proximal end that does not have an insulative coating and thus is electrically conductive. Making electrical contact with the proximal end of the guidewire may allow the guidewire to be used for pacing.

The pacing tool 10 includes a tool body 14. The tool body 14 may be formed of an electrically insulative material such as a polymer, for example. Any of a variety of different polymers may be used. The tool body 14 defines an elongate cavity 16 that extends within the tool body 14. It will be appreciated that the elongate cavity 16 may be adapted to accommodate a guidewire extending therein. In some instances, the elongate cavity 16 may include an enlarged-diameter mouth 18 that is larger in diameter than the rest of the elongate cavity 16. In some instances, this can facilitate advancing a guidewire into the elongate cavity 16. The elongate cavity 16 extends from the enlarged-diameter mouth 18 to a proximal end 20.

In some instances, the elongate cavity 16 may have a diameter that is slightly larger than the diameter of any guidewire that is expected to be used with the pacing tool 10. As an example, the elongate cavity 16 may have a diameter that is within 1 percent, or within 0.5 percent, or within 0.1 percent of the diameter of any guidewire that is expected to be used with the pacing tool 10. In some instances, this allows for a frictional fit between the elongate cavity 16 and the guidewire that holds the guidewire in position within the elongate cavity 16. In some instances, the tool body 14 may be formed of an elastomeric material that can stretch in response to a guidewire being inserted into the elongate cavity 16. When the pacing tool 10 is formed of an elastomeric material, the elongate cavity 16 may have a relaxed diameter that is less than the diameter of any guidewire that is expected to be used with the pacing tool 10, such as a relaxed diameter that is within 5 percent of the diameter of any guidewire that is expected to be used with the pacing tool 10, or within 2 percent, or within 1 percent of the diameter of any guidewire that is expected to be used with the pacing tool 10.

In some instances, the elongate cavity 16 may have a diameter that is greater than the diameter of any guidewire that is expected to be used with the pacing tool 10, in order to allow the guidewire (or the proximal region thereof) to be easily inserted into the pacing tool 10. In some instances, the pacing tool 10 may include additional structure that allows the guidewire to be held in place within the elongate cavity 16. The tool body 14 defines a channel 22 that extends orthogonally from the elongate cavity 16. The channel 22 is adapted to accommodate a guidewire holder 24 that is adapted to translate within the channel 22.

In some instances, as shown, the guidewire holder 24 includes a gripper 26 that is adapted to releasably engage a guidewire disposed within the elongate cavity 16. In some instances, the gripper 26 may have a textured lower surface 28. In some instances, the gripper 26 may be an elastomeric material that can deform when pushed into contact with a guidewire. A plunger 30 extends out of the channel 22 such that the plunger 30 may be engaged by hand. The plunger 30 is adapted to be pushed in order to releasably engage the gripper 26 with the guidewire. In some instances, the guidewire holder 24 includes a spring 32 that extends between the gripper 26 and the plunger 30. The spring 32 may be adapted to compress in response to a user pushing downward (in the illustrated orientation) on the plunger 30. As the user pushes down, the gripper 26 will move downward and into contact with the guidewire. As the user continues to push down, and depending on how hard the user pushes down, the spring 32 may compress to absorb the additional applied force.

The guidewire holder 24 shown in FIG. 1 is an example of how the guidewire may be held in position. As another example, the channel 22 and the guidewire holder 24 may be adapted to include several detents or other features (not shown) that allow the guidewire holder 24 to be pressed down (in the illustrated orientation) a first time to lock the guidewire holder 24 in position against a guidewire. The guidewire holder 24 may be pressed a second time to unlock the guidewire holder 24, and to allow the guidewire holder 24 to retract from contact with the guidewire. As another example, the channel 22 may have a threaded inner surface that engages a corresponding threaded outer surface of the guidewire holder. The guidewire holder may be rotated a first direction in order to drive the guidewire holder down (in the illustrated orientation) into contact with the guidewire and may be rotated a second, opposing, direction in order to retract the guidewire holder from the guidewire. As an example, the guidewire holder may be rotated clockwise in order to drive the guidewire holder towards the guidewire and the guidewire holder may be rotated counter-clockwise in order to drive the guidewire holder away from the guidewire.

The pacing tool 10 includes a compressible electrical contact 34 that is disposed at the proximal end 20 of the elongate cavity 16. In some instances, the compressible electrical contact 34 is adapted to shorten axially when a guidewire is pushed proximally into the elongate cavity 16. A cable 36 is electrically coupled with the compressible electrical contact 34 and is adapted to be electrically coupled with the pacing system 12. Thus, electrical pacing pulses generated by the pacing system 12 may be transmitted via the cable 36 to the compressible electrical contact 34 and hence to the guidewire. In some instances, the compressible electrical contact 34 may be considered as being a spring-loaded pin or a pogo pin, and may be referred to herein by any of these terms.

In some cases, the compressible electrical contact 34 includes a barrel element 36 that is adapted to be secured to the proximal end 20 of the elongate cavity 16. In some instances, the barrel element 38 may be electrically coupled with the cable 36. A plunger element 40 is slidingly disposed within the barrel element 38 and extends distally from the barrel element 38. A spring 42 is disposed between the barrel element 38 and the plunger element 40. The spring 42 is adapted to bias the plunger element 38 distally relative to the barrel element 40 but to allow the plunger element 40 to move proximally relative to the barrel element 38 in response to the guidewire being pushed against the compressible electrical contact. In some instances, the plunger element 40 is held captive relative to the barrel element 38 by an annular flange 44 formed at a distal end of the barrel element 38.

The barrel element 38 and the plunger element 40 are both formed of electrically conductive materials such as a metal. The barrel element 38 and the plunger element 40 are electrically coupled together. While in some instances electrical energy may be transmitted through the compressible electrical contact 34 via the spring 42, in some instances the spring 42 has a higher resistance than the plunger element 40, and thus it is beneficial for the plunger element 40 to be in electrical contact with the barrel element 38. In some instances, the plunger element 40 may be designed to tilt slightly relative to the barrel element 38 in order to maintain electrical contact between the plunger element 40 and the barrel element 38. In some instances, the barrel element 38 and the plunger element 40 may each be formed of brass or copper, and may include coatings such as nickel or even gold. In some instances, the spring 42 may be formed of copper alloys or spring steel. The spring 42 provides a constant biasing force, resisting proximal movement of the plunger element 40.

Figure 2:
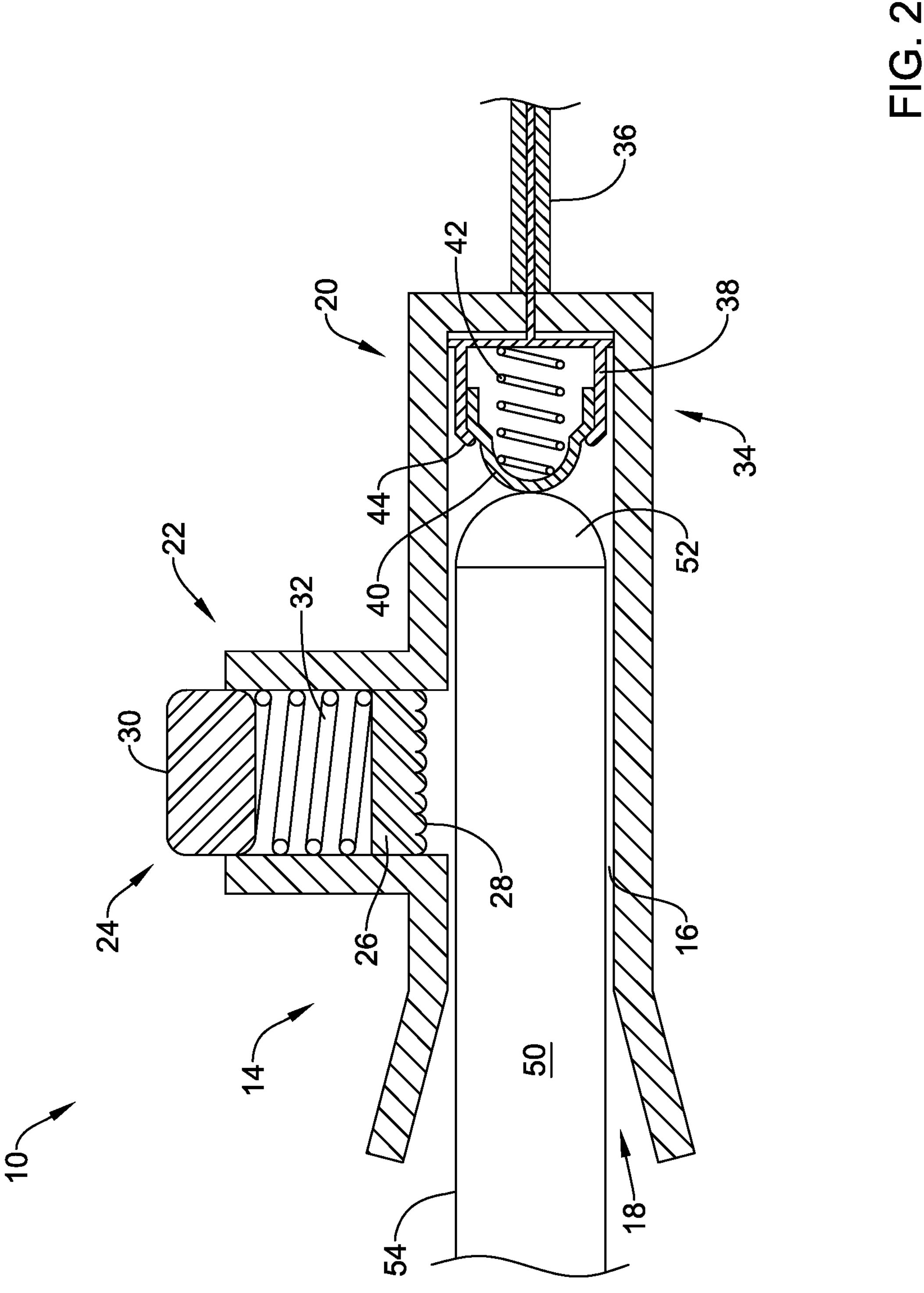
FIG. 2 is a schematic view of the illustrative pacing tool of FIG. 1, with a guidewire inserted into the pacing tool.
Figure 3:
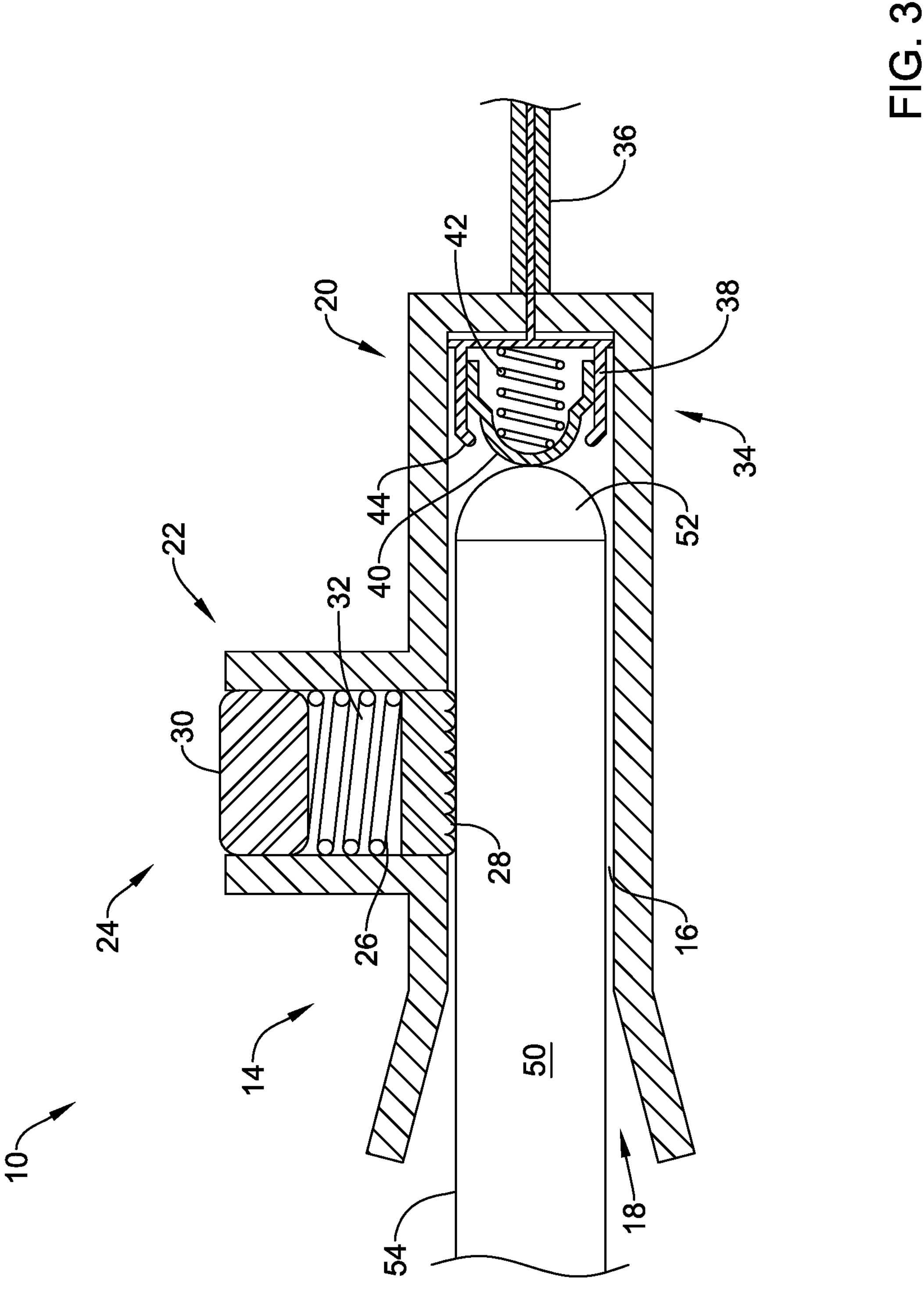
FIG. 3 is a schematic view of the illustrative pacing tool of FIG. 1, with the guidewire fully inserted into the pacing tool.

FIGS. 2 and 3 show how the pacing tool 10 operates. The pacing system 12 is not shown in FIGS. 2 and 3. In FIG. 2, the proximal portion of a guidewire 50 has been inserted into the elongate cavity 16. A proximal end 52 of the guidewire 50 is just contacting the plunger element 40 of the compressible electrical contact 34. The guidewire holder 24 has not yet been actuated into contact with the guidewire 50. In FIG. 3, however, the guidewire 50 has been urged farther into the elongate cavity 16 such that the plunger element 40 has moved proximally relative to the barrel element 38 as the spring 42 has compressed somewhat. This means that the spring 42 is providing a biasing force urging the plunger element 40 distally, which helps to maintain a constant electrical contact between the proximal end 52 of the guidewire 50 and the plunger element 40. FIG. 3 also shows actuation of the guidewire holder 24. The plunger 30 has been moved downward (in the illustrated orientation), thereby pushing the gripper 26 towards the guidewire 50 such that the textured lower surface 28 has contacted an outer surface 54 of the guidewire 50. By keeping a downward pressure on the plunger 30, the gripper 26 is maintained in contact with the outer surface 54 of the guidewire 50 and thus the guidewire 50 is held in place with electrical contact being maintained between the proximal end 52 of the guidewire 50 and the compressive electrical contact 34. In some instances, the spring 42 may compress, depending on how much pressure a user is maintaining on the plunger 30.

Figure 4:
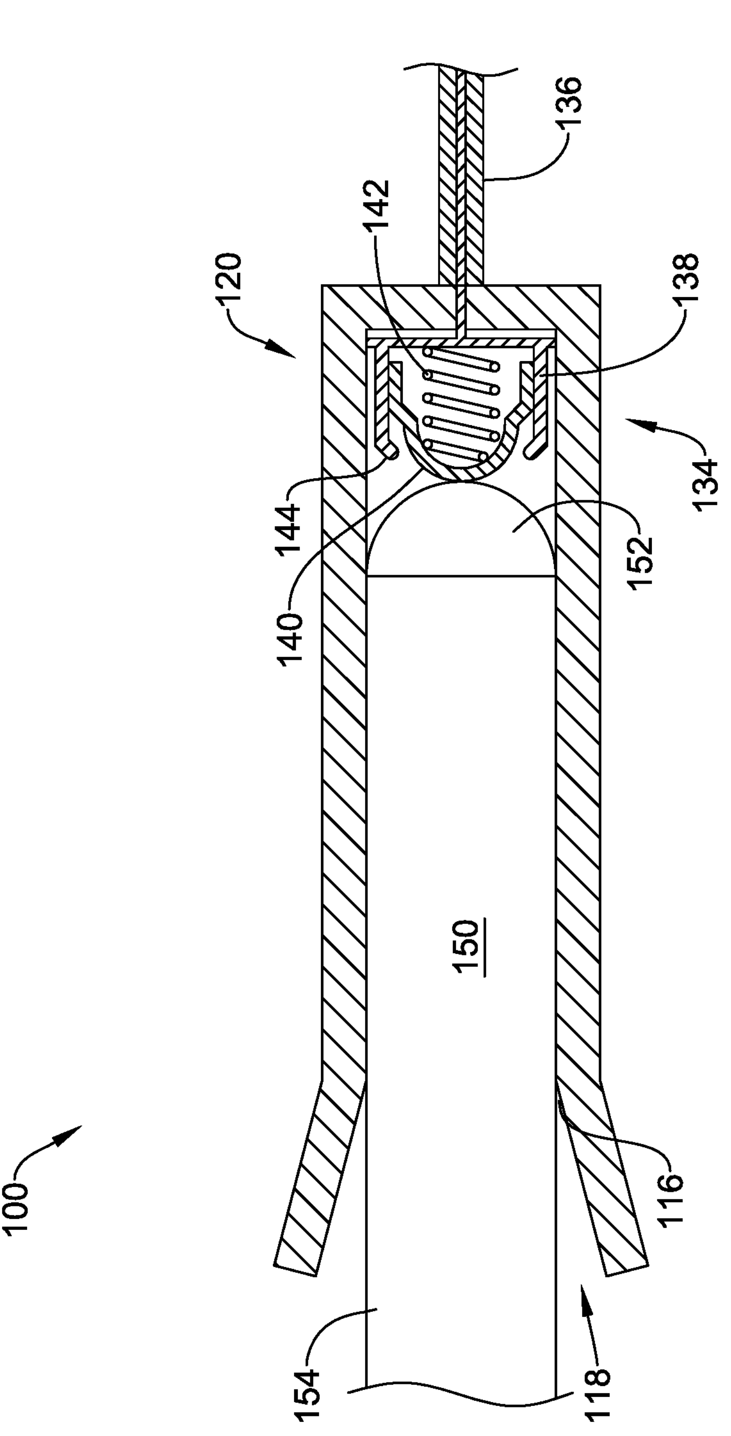
FIG. 4 is a schematic tool of an illustrative pacing tool, showing a guidewire fully inserted into the pacing tool.

As noted, in some instances, the elongate cavity 16 may be more closely dimensioned relative to an outer diameter of any guidewire 50 that is used with the pacing tool. FIG. 4 is a schematic view of an illustrative pacing tool 100 that may be used to form a temporary electrical connection between a guidewire (not shown in FIG. 1) and the pacing system 12. The pacing tool 100 is adapted to releasably receive a proximal end 152 of a guidewire 150 and to make electrical contact with the proximal end 152 of the guidewire 150. In some cases, the pacing tool 100 may be adapted to provide an electrical connection with the proximal end 152 of the guidewire 150. While many guidewires include insulative coatings over various portions of the guidewire, some guidewires have a proximal end that does not have an insulative coating and thus is electrically conductive. Making electrical contact with the proximal end of the guidewire may allow the guidewire to be used for pacing.

The pacing tool 100 includes a tool body 114. The tool body 114 may be formed of an electrically insulative material such as a polymer, for example. Any of a variety of different polymers may be used. The tool body 114 defines an elongate cavity 116 that extends within the tool body 114. In some instances, the elongate cavity 116 may include an enlarged-diameter mouth 118 that is larger in diameter than the rest of the elongate cavity 116. In some instances, this can facilitate advancing the guidewire 150 into the elongate cavity 116. The elongate cavity 116 extends from the enlarged-diameter mouth 118 to a proximal end 120.

In some instances, the elongate cavity 116 may have a diameter that is slightly larger than the diameter of the guidewire 150. As an example, the elongate cavity 116 may have a diameter that is within 1 percent, or within 0.5 percent, or within 0.1 percent of the diameter of the guidewire 150. In some instances, this allows for a frictional fit between the elongate cavity 116 and an outer surface 154 of the guidewire 150 that holds the guidewire 150 in position within the elongate cavity 116. In some instances, the tool body 114 may be formed of an elastomeric material that can stretch in response to the guidewire 150 being inserted into the elongate cavity 116. When the pacing tool 100 is formed of an elastomeric material, the elongate cavity 116 may have a relaxed diameter that is less than the diameter of the guidewire 150, such as a relaxed diameter that is within 5 percent of the diameter of the guidewire 150, or within 2 percent, or within 1 percent of the diameter of the guidewire 150.

The pacing tool 100 includes a compressible electrical contact 134 that is disposed at the proximal end 120 of the elongate cavity 116. In some instances, the compressible electrical contact 134 is adapted to shorten axially when a guidewire is pushed proximally into the elongate cavity 116. A cable 136 is electrically coupled with the compressible electrical contact 134 and is adapted to be electrically coupled with the pacing system 12. Thus, electrical pacing pulses generated by the pacing system 12 may be transmitted via the cable 136 to the compressible electrical contact 134 and hence to the guidewire 150. In some instances, the compressible electrical contact 134 may be considered as being a spring-loaded pin or a pogo pin, and may be referred to herein by any of these terms.

In some cases, the compressible electrical contact 134 includes a barrel element 136 that is adapted to be secured to the proximal end 120 of the elongate cavity 116. In some instances, the barrel element 138 may be electrically coupled with the cable 136. A plunger element 140 is slidingly disposed within the barrel element 138 and extends distally from the barrel element 138. A spring 142 is disposed between the barrel element 138 and the plunger element 140. The spring 142 is adapted to bias the plunger element 138 distally relative to the barrel element 140 but to allow the plunger element 140 to move proximally relative to the barrel element 138 in response to the guidewire being pushed against the compressible electrical contact. In some instances, the plunger element 140 is held captive relative to the barrel element 138 by an annular flange 144 formed at a distal end of the barrel element 138.

The barrel element 138 and the plunger element 140 are both formed of electrically conductive materials such as a metal. The barrel element 138 and the plunger element 140 are electrically coupled together. While in some instances electrical energy may be transmitted through the compressible electrical contact 134 via the spring 142, in some instances the spring 142 has a higher resistance than the plunger element 140, and thus it is beneficial for the plunger element 140 to be in electrical contact with the barrel element 138. In some instances, the plunger element 140 may be designed to tilt slightly relative to the barrel element 138 in order to maintain electrical contact between the plunger element 140 and the barrel element 138. In some instances, the barrel element 138 and the plunger element 140 may each be formed of brass or copper, and may include coatings such as nickel or even gold. In some instances, the spring 142 may be formed of copper alloys or spring steel. The spring 142 provides a constant biasing force, resisting proximal movement of the plunger element 140.

In FIG. 4, the guidewire 150 is shown as having been urged farther into the elongate cavity 116 such that the plunger element 140 has moved proximally relative to the barrel element 138 as the spring 142 has compressed somewhat. This means that the spring 142 is providing a biasing force urging the plunger element 140 distally, which helps to maintain a constant electrical contact between the proximal end 152 of the guidewire 150 and the plunger element 140.

Figures 5, 6, 7, 8:
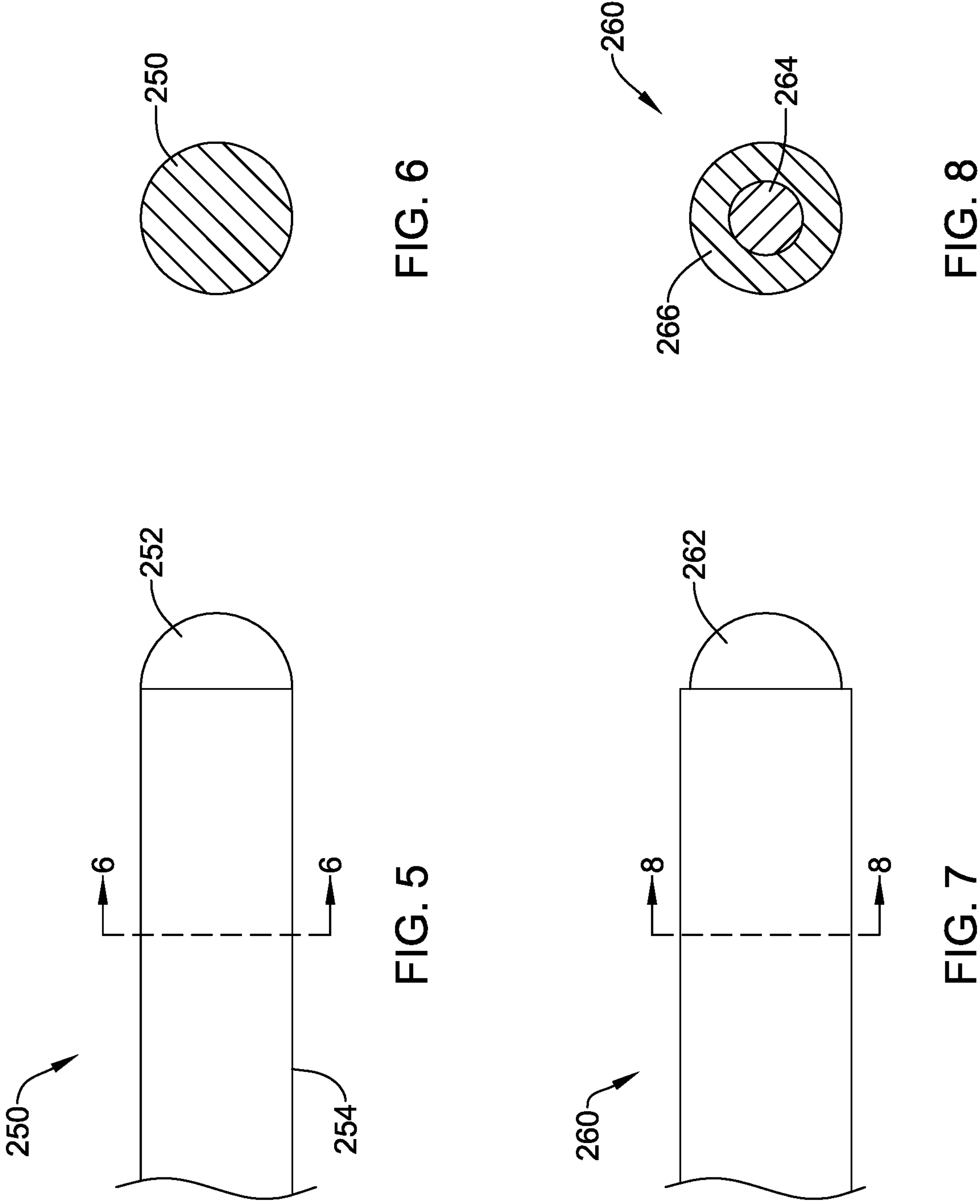
FIG. 5 is a schematic side view of a proximal portion of an illustrative guidewire usable with the illustrative pacing tools of FIGS. 1 to 4.
FIG. 6 is a cross-sectional view of the illustrative guidewire of FIG. 5, taken along the line 6-6 thereof.
FIG. 7 is a schematic side view of a proximal portion of an illustrative guidewire usable with the illustrative pacing tools of FIGS. 1 to 4.
FIG. 8 is a cross-sectional view of the illustrative guidewire of FIG. 6, taken along the line 8-8 thereof.

A variety of different guidewires may be used with the pacing tool 10 and the pacing tool 100, as long as a proximal end of the guidewire is electrically conductive. FIGS. 5 through 9 provide schematic views of several different guidewires that may be used in combination with the pacing tool 10 and the pacing tool 100. FIG. 5 is a schematic side view of a proximal portion of a guidewire 250. The guidewire 250 has an electrically conductive proximal end 252 and an outer surface 254. As can be seen in FIG. 6, which is a cross-sectional view of the guidewire 250 taken along the line 6-6 of FIG. 5, the guidewire 250 (or at least the proximal portion thereof) is not insulated and may be considered as being a bare metal guidewire.

FIG. 7 is a schematic side view of a proximal portion of a guidewire 260. The guidewire 260 has an electrically conductive proximal end 262. In some cases, the guidewire 260 may have a larger diameter (distal of the proximal end 262) as a result of an insulative layer over the guidewire 260 (but not extending over the proximal end 262). As can be seen in FIG. 8, which is a cross-sectional view of the guidewire 260 taken along the line 8-8 of FIG. 7, the guidewire 260 (or at least the proximal portion thereof) includes a core member 264 and an insulative layer 266 surrounding the core member 264. In some instances the core member 264 is electrically conductive and thus may be electrically coupled with the proximal end 262.

Figure 9:
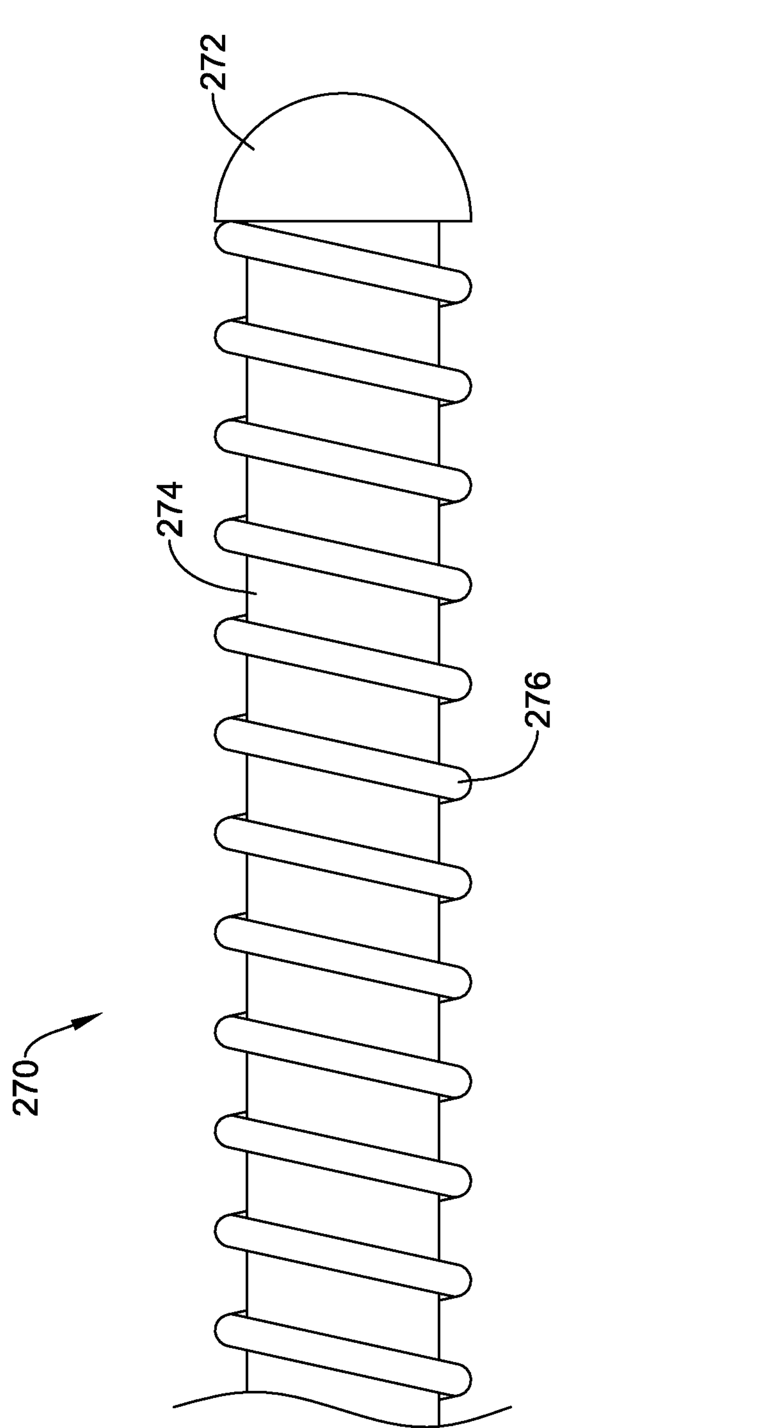
FIG. 9 is a side view of a proximal portion of an illustrative guidewire usable with the illustrative pacing tools of FIGS. 1 to 4.

FIG. 9 is a schematic side view of a proximal portion of a guidewire 270. The guidewire 270 has an electrically conductive proximal end 272. Distal of the proximal end 272, the guidewire 270 includes a core member 274. The core member 274 may be insulated or uninsulated. In some instances, the core member 274 has a reduced diameter relative to that of the proximal end 272 in order to accommodate a coil 276 that extends over the core member 274.

Each of the guidewire 250, the guidewire 260 and the guidewire 270 provide examples of guidewires that may be used as pacing guidewires in combination with the pacing tool 10 and the pacing tool 100. Inclusion of an electrically conductive proximal end 252, 262, 272 allows these guidewires 250, 260, 270 to be used for pacing. In some instances, rather than having a semicircular proximal tip, the proximal end 252, 262, 272 may be partially insulated as long as there is an opening formed in the insulation that would allow electrical contact with the compressive electrical contact 34, 134 in the pacing tool 10, 100.

Some mammalian hearts (e.g., human, etc.) include four heart valves: a tricuspid valve, a pulmonary valve, an aortic valve, and a mitral valve. Some relatively common medical conditions may include or be the result of inefficiency, ineffectiveness, or complete failure of one or more of the valves within the heart. Treatment of defective heart valves poses other challenges in that the treatment often requires the repair or outright replacement of the defective valve. Such therapies may be highly invasive to the patient. Disclosed herein are medical devices and/or procedures that may be used within a portion of the cardiovascular system in order to diagnose, treat, and/or repair the system, for example during and/or in conjunction with a TAVI or TAVR procedure, or in place of a TAVI or TAVR procedure in patients not suitable for such. At least some of the medical devices and/or procedures disclosed herein may be delivered and/or performed percutaneously and, thus, may be much less invasive to the patient, although other surgical methods and approaches may also be used. The devices disclosed herein may also provide a number of additional desirable features and benefits as described in more detail below. For the purpose of this disclosure, the discussion below is directed toward the treatment of a native aortic valve and will be so described in the interest of brevity. This, however, is not intended to be limiting as the skilled person will recognize that the following discussion may also apply to a mitral valve or another heart valve with no or minimal changes to the structure and/or scope of the disclosure. Similarly, the medical devices and/or procedures disclosed herein may have applications and uses in other portions of a patient's anatomy, such as but not limited to, arteries, veins, and/or other body lumens.

Figure 10:
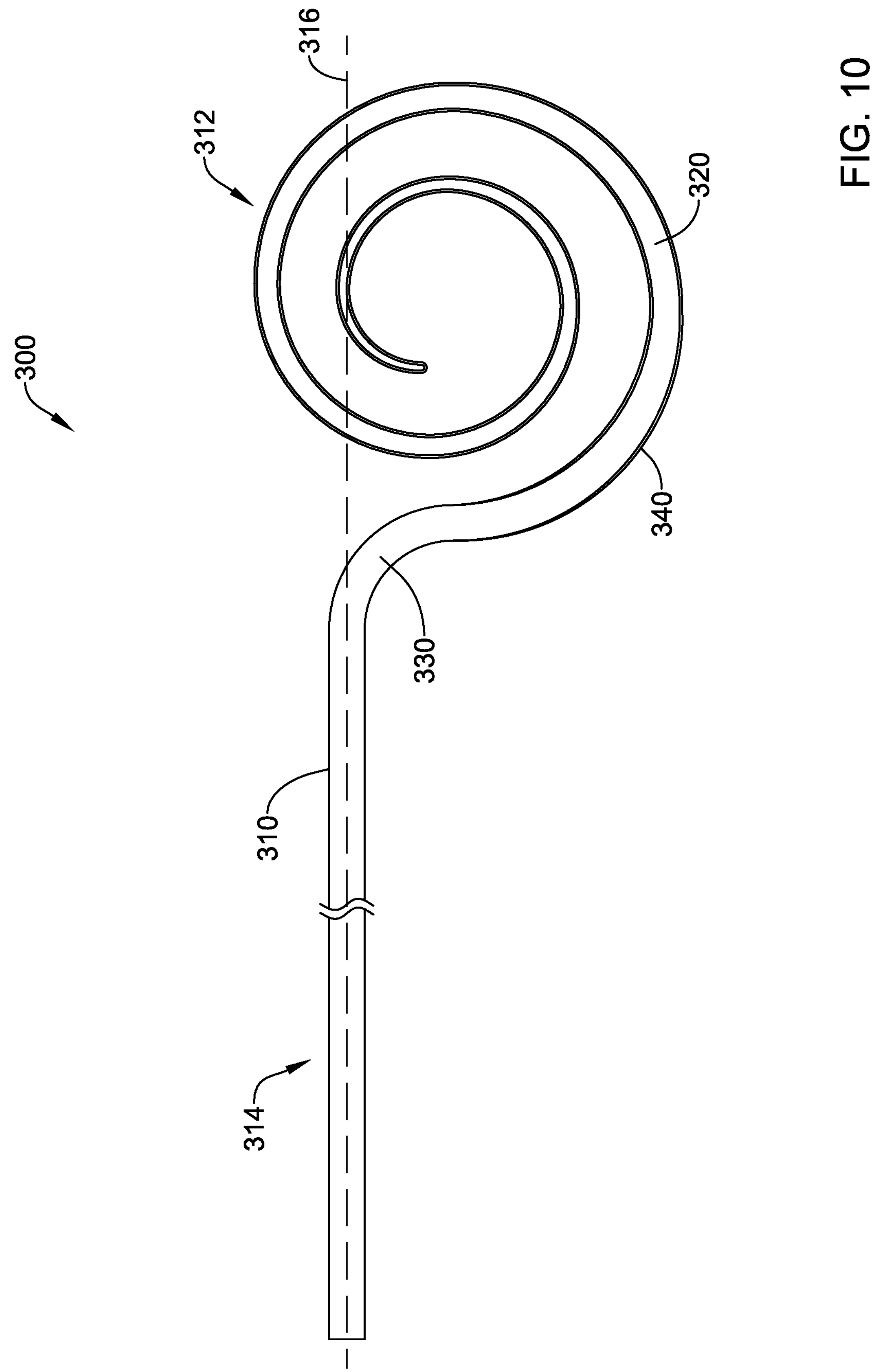
FIG. 10 is a schematic view of an illustrative guidewire.

FIG. 10 is a schematic view of an illustrative guidewire 300 for delivering a replacement heart valve to a native heart valve. In some instances, the guidewire 300 may also be adapted to allow its use in delivering pacing pulses to the heart during the process of delivering the replacement heart valve. In some instances, the guidewire 300 may include an elongate shaft 310 including a distal section 312 and a proximal section 314 extending proximally from the distal section 312. In some instances, the proximal section 314 may define a central longitudinal axis 316, which may be projected distally of the proximal section 314 for reference.

The elongate shaft 310 may include a coiled portion 320 disposed within the distal section 312 in an unbiased and/or unconstrained state, wherein the coiled portion 320 of the elongate shaft 310 is curved in a first direction in a first plane, as viewed proximally to distally. In some instances, the coiled portion 320 may be curved in the first direction in the first plane in a distal direction along the elongate shaft 310. In some instances, the coiled portion 320 may extend, from proximal to distal along the length of the elongate shaft 310, in the first direction in the first plane. In some instances, the central longitudinal axis 316 may be disposed within the first plane. Other configurations are also contemplated. In some instances, the first direction may be counterclockwise. In some instances, the first direction may be clockwise.

In some instances, the elongate shaft 310 may include a reverse curve portion 330 curved in a second direction opposite the first direction in the unbiased and/or unconstrained state, as viewed proximally to distally. In some instances, the reverse curve portion 330 may be disposed within and/or may be curved in the second direction within the first plane. In some instances, the reverse curve portion 330 may be curved in the second direction in the first plane in the distal direction along the elongate shaft 310. In some instances, the reverse curve portion 330 may extend, from proximal to distal along the length of the elongate shaft 310, in the second direction in the first plane. In some instances where the first direction is counterclockwise, the second direction may be clockwise. In some instances where the first direction is clockwise, the second direction may be counterclockwise. In at least some instances, the reverse curve portion 330 may be disposed proximal of the coiled portion 320 of the elongate shaft 310.

In some instances, the reverse curve portion 330 may be at least partially disposed in the proximal section 314 of the elongate shaft 310. In some instances, the reverse curve portion 330 may extend from a distal portion of the proximal section 314 of the elongate shaft 310 into the distal section 312 of the elongate shaft 310. In some instances, the reverse curve portion 330 may span a joint and/or a transition region between the proximal section 114 of the elongate shaft 310 and the distal section 312 of the elongate shaft 310. In some instances, the reverse curve portion 330 may be disposed entirely within the proximal section 314 of the elongate shaft 310.

In some instances, the coiled portion 320 of the elongate shaft 310 may extend laterally on opposing sides of a second plane containing the central longitudinal axis 316 of the proximal section 314 of the elongate shaft 310 in the unbiased and/or unconstrained state. In some instances, a first portion of the coiled portion 320 of the elongate shaft 310 may be disposed on a first side of the second plane containing the central longitudinal axis 316 of the proximal section 314 of the elongate shaft 310, and a second portion of the coiled portion 320 of the elongate shaft 310 may be disposed on a second side of the second plane containing the central longitudinal axis 316 of the proximal section 314 of the elongate shaft 310, wherein the second side of the second plane is opposite the first side of the second plane relative to the second plane. In some instances, the second plane may be oriented at an oblique angle to the first plane. In at least some instances, the second plane may be oriented substantially perpendicular to the first plane.

In some instances, the elongate shaft 310 may have a selected level of axial stiffness and/or pushability characteristics while also having a selected level of lateral stiffness and/or flexibility to permit navigation through the patient's vasculature. In some instances, the proximal section 314 of the elongate shaft 310 may be laterally stiffer than the distal section 312 of the elongate shaft 310. In some instances, the distal section 312 may be more flexible than the proximal section 314 of the elongate shaft 310. Other configurations are also contemplated.

In some instances, the distal section 312 of the elongate shaft 310 may be tapered radially inwardly in a distal direction. For example, a proximal portion of the distal section 312 of the elongate shaft may have an outer diameter that is greater than an outer diameter of a distal portion of the distal section 312. In some instances, the distal section 312 of the elongate shaft 310 may be tapered radially inwardly from the proximal section 314 of the elongate shaft 310 to a distalmost tip of the elongate shaft 310. In some instances, the distal section 312 of the elongate shaft 310 may be tapered continuously in the distal direction. In some instances, the distal section 312 of the elongate shaft 310 may be tapered in a stepwise fashion in the distal direction. In some instances, at least a portion of the coiled portion 320 may be tapered radially inwardly in the distal direction. In some instances, an entirety of the coiled portion 320 may be tapered radially inwardly in the distal direction.

In some instances, the elongate shaft 310 may include and/or may be formed from a metallic material. In some instances, the elongate shaft 310 is formed from stainless steel. Other configurations are also contemplated. Some suitable but non-limiting examples of materials for the elongate shaft 310 are discussed below. In some instances, the elongate shaft 310 may include a polymeric coating 340 disposed on the coiled portion 320 of the elongate shaft 310 and/or the distal section 312 of the elongate shaft 310. In at least some instances, the proximal section 314 of the elongate shaft 310 may be devoid of the polymeric coating 340. Some suitable but non-limiting examples of materials for the polymeric coating are discussed below.

As noted, the guidewire 300 may be used for delivering and implanting a replacement cardiac valve within a patient. In some instances, the guidewire 300 may be adapted to also be able to be used for pacing the heart during the replacement valve implantation process. FIGS. 11 through 16 provide an illustrative but non-limiting example of using the guidewire 100 for delivery and implantation of a replacement cardiac valve while optionally using the guidewire 300 to deliver pacing pulses during the implantation process. FIGS. 11 through 16 include a schematic view of some of the cardiac anatomy of a patient's heart 410. The anatomy includes an aortic valve 412 having valve leaflets 414, a left ventricle 416, and certain connected vasculature, such as the aorta 420 connected to the aortic valve 412 of the patient's heart 410 by the aortic arch 422, the coronary arteries 424, the ostia 423 of the coronary arteries 424, and other large arteries 426 (e.g., subclavian arteries, carotid arteries, brachiocephalic artery) that extend from the aortic arch 422 to important internal organs. The discussion herein is directed toward use in treating the aortic valve 412 and will be so described in the interest of brevity. This, however, is not intended to be limiting as the skilled person will recognize that the following discussion may also apply to other heart valves, vessels, and/or treatment locations within a patient with no or minimal changes to the structure and/or scope of the disclosure.

Figure 11:
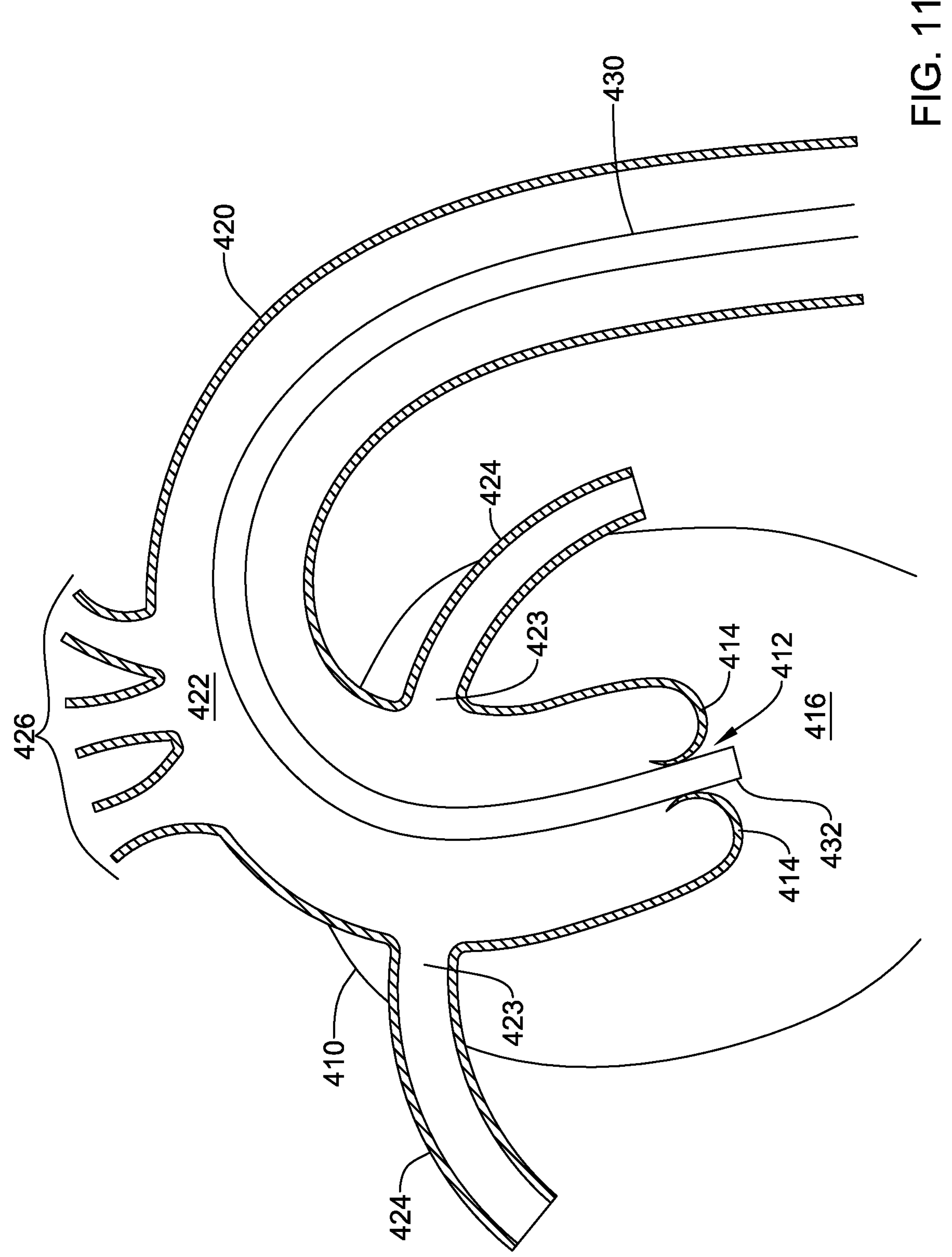
FIGS. 11 through 16 are schematic views showing a method of pacing while delivering a replacement heart valve implant using the illustrative guidewire of FIG. 10.

As seen in FIG. 11, a catheter 300 may be advanced through the patient's vasculature (e.g., the aorta 420, etc.) to and/or through the native heart valve (e.g., the aortic valve 412) into the ventricle 416 of the patient's heart 410. A distal end 432 of the catheter 430 may be disposed within the ventricle 416 of the patient's heart 410. The catheter 430 may include one or more lumens extending through the catheter 430 to the distal end 432. At least one of the one or more lumens may be a guidewire lumen and/or a working lumen. In some embodiments, the patient's heart 410 may be accessed more directly and navigation through the patient's vasculature (e.g., the aorta 420) may not be necessary.

Figure 12:
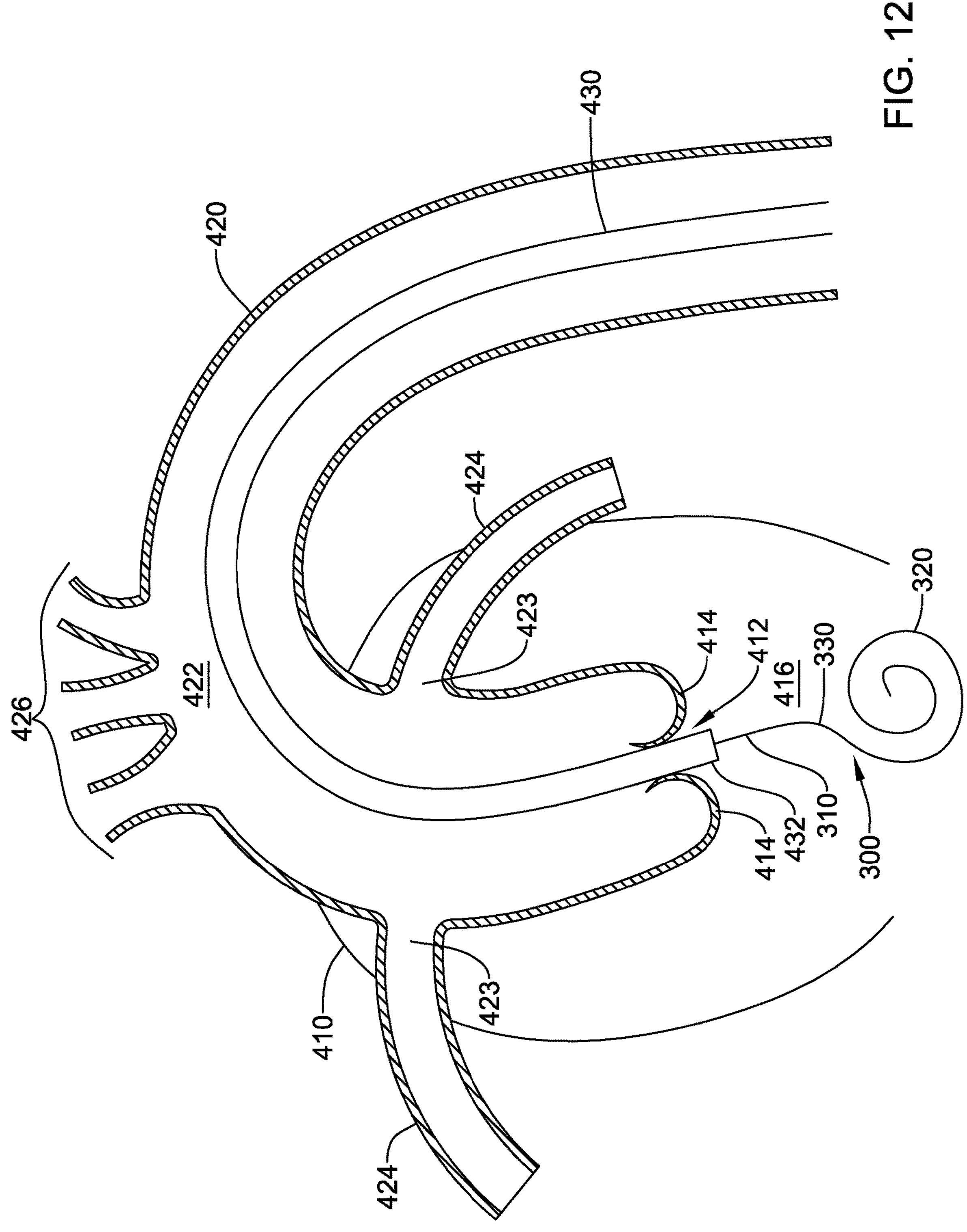

In some instances, the guidewire 300 may be advanced out the distal end 432 of the catheter 430 into the ventricle 416 of the patient's heart, as seen in FIG. 12. The guidewire 100 may be configured as described herein. In some instances, the guidewire 300 may be contained and/or constrained in a straightened configuration within the one or more lumens of the catheter 430 as the catheter 430 is advancing to the native heart valve (e.g., the aortic valve 412) of the patient's heart 410. In some instances, the guidewire 300 may be advanced simultaneously with and/or within the catheter 430 through the patient's vasculature to the native heart valve (e.g., the aortic valve 412) of the patient's heart 410. In some instances, the guidewire 300 may be advanced through the catheter 430 after positioning the distal end 432 of the catheter 430 within the ventricle 416 of the patient's heart 410.

Figure 13:
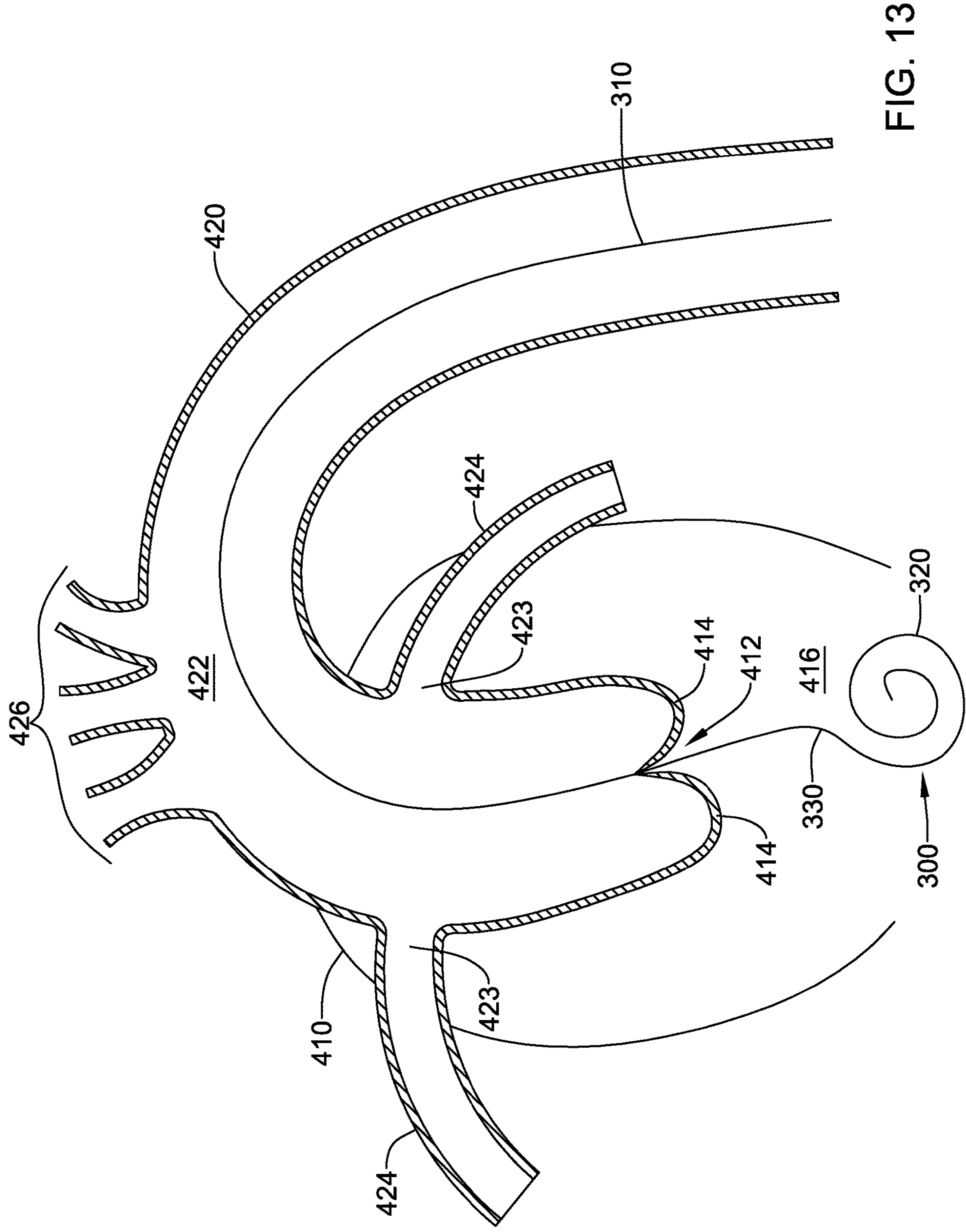

The coiled portion 320 of the guidewire 300 may be disposed within the ventricle 416 of the patient's heart 410 such that the distal portion of the proximal section 314 is spaced radially inward from an ostium of the native heart valve (e.g., the aortic valve 412) when the coiled portion 320 of the elongate shaft 310 of the guidewire 300 is positioned within the ventricle 416 of the patient's heart 410. The catheter 430 may be removed while maintaining the coiled portion 320 of the guidewire 300 within the ventricle 416 of the patient's heart 410, as shown in FIG. 13. FIG. 13 also illustrates the elongate shaft 310 spaced radially inwardly from the ostium of the native heart valve (e.g., the aortic valve 412) when the coiled portion 320 of the elongate shaft 310 of the guidewire 300 is positioned within the ventricle 416 of the patient's heart 410. The reverse curve portion 330 urges the distal portion of the proximal section 314 of the elongate shaft 310 toward a center of the native heart valve (e.g., the aortic valve 412).

Figure 14:
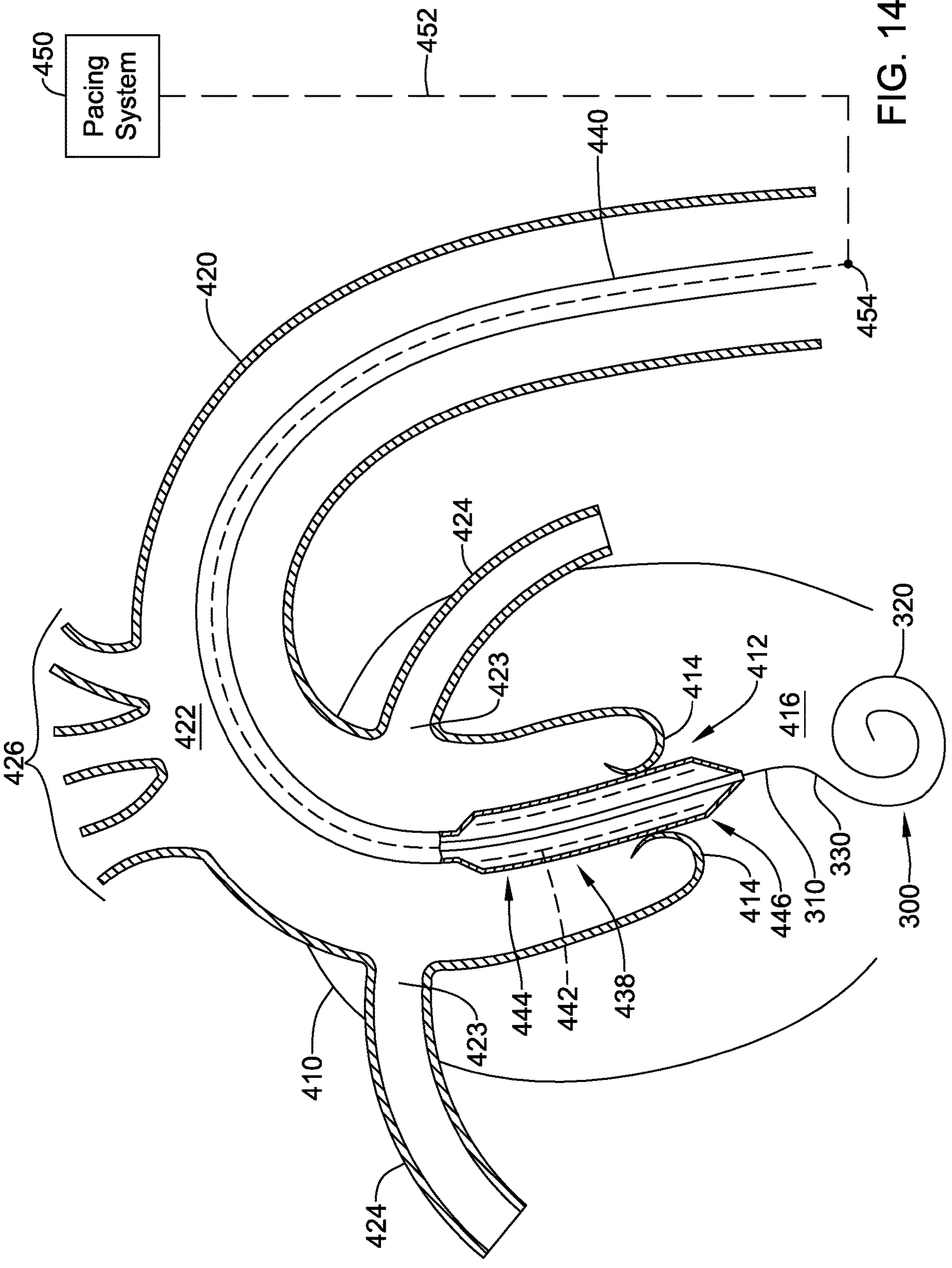

In some instances, a deployment device 440 may be advanced over the guidewire 300 to the native heart valve (e.g., the aortic valve 412) of the patient's heart 410, as seen in FIG. 14. The deployment device 440 is shown in a partial cutaway view. In some instances, the deployment device 440 may include an outer sheath and an inner shaft axially translatable relative to the outer sheath. In some instances, the inner shaft of the deployment device 440 may include a central guidewire lumen extending therethrough to a distal end of the deployment device 440.

The deployment device 440 and/or the outer sheath may include a distal containment section 438 having a replacement heart valve implant 442 disposed therein in a constrained and/or collapsed configuration. The distal containment section 438 may include a proximal portion 444 and a distal portion 446. In some instances, the proximal portion 444 and the distal portion 446 of the distal containment section 438 may be configured to axially translate relative to each other to open the distal containment section and release the replacement heart valve implant 442.

In some instances, the proximal portion 444 of the distal containment section 438 may be fixedly attached to and/or integrally formed with the outer sheath. In some instances, the distal portion 446 of the distal containment section 438 may be fixedly attached to and/or integrally formed with the inner shaft. Therefore, relative axial translation between the outer sheath and the inner shaft may cause corresponding relative axial translation of the proximal portion 444 of the distal containment section 438 and the distal portion 446 of the distal containment section 438 to open the distal containment section 438 and release the replacement heart valve implant 442. The distal containment section 438 of the deployment device 440 may be positioned adjacent to and/or within the native heart valve (e.g., the aortic valve 412) prior to opening the distal containment section 438 of the deployment device 440. In at least some instances, the distal portion 446 of the distal containment section 438 may be disposed at least partially upstream of the native heart valve (e.g., the aortic valve 412) and/or at least partially within the ventricle 416 of the patient's heart 410 prior to opening the distal containment section 438 of the deployment device 440.

Figure 15:
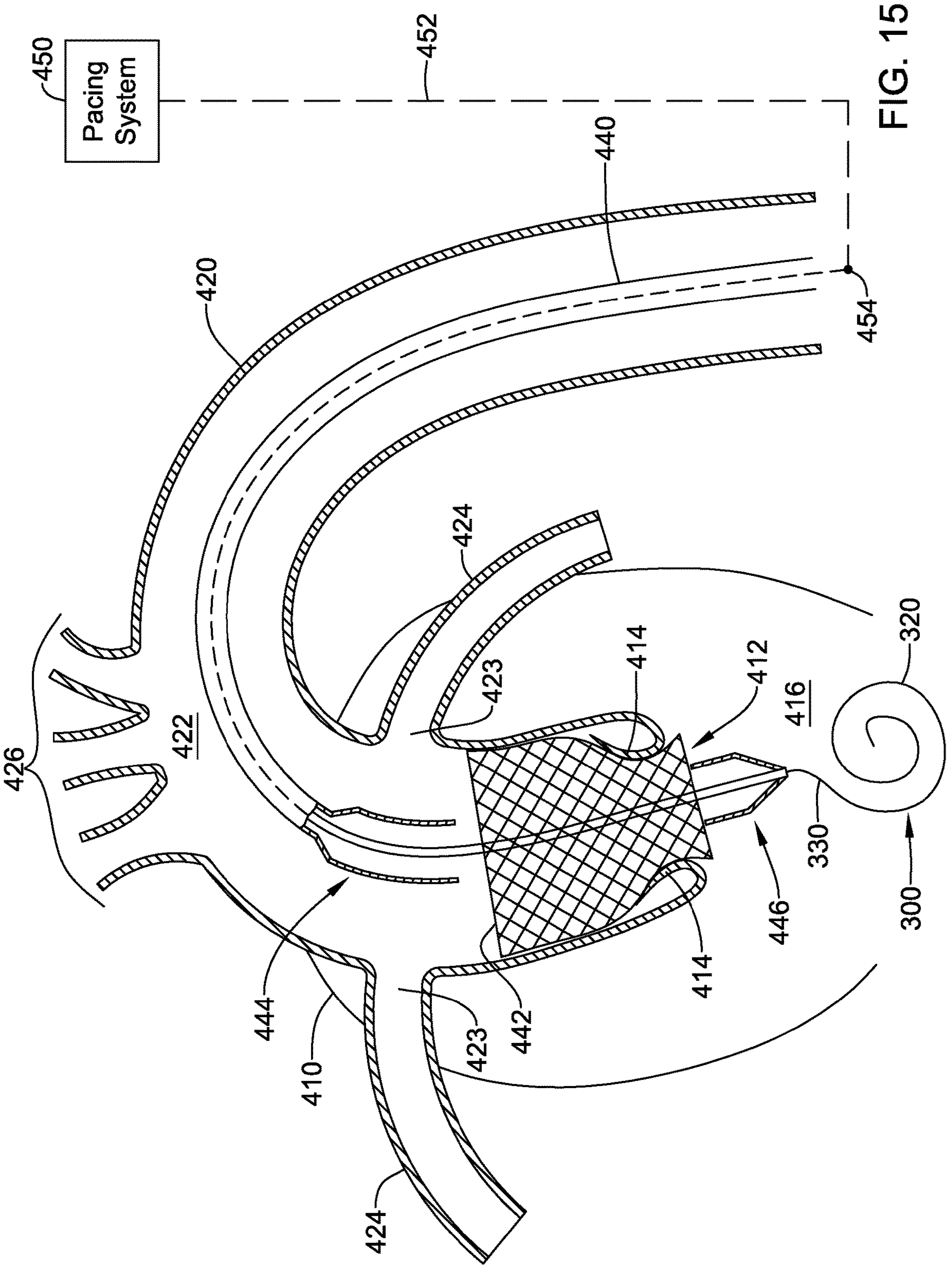

In some instances, the replacement heart valve implant 442 may be deployed within the native heart valve (e.g., the aortic valve 412) by opening the distal containment section 438 of the deployment device 440 while the distal containment section 438 is disposed within the native heart valve (e.g., the aortic valve 412), as seen in FIG. 15. The replacement heart valve implant 442 may include an expandable framework and a plurality of valve leaflets disposed within the expandable framework. In some instances, the expandable framework may be self-expanding. In some instances, the expandable framework may be mechanically and/or balloon expandable. Other configurations are also contemplated.

After opening the distal containment section, the distal portion 446 of the distal containment section 438 may be disposed upstream of the native heart valve (e.g., the aortic valve 412) and/or within the ventricle 416 of the patient's heart 410 and the proximal portion 444 of the distal containment section 438 may be disposed downstream of the native heart valve (e.g., the aortic valve 412) and/or within the aortic arch 422 and/or the aorta 420 of the patient. The reverse curve portion 330 of the elongate shaft 310 of the guidewire 300 may be at least partially disposed distal and/or upstream of the native heart valve (e.g., the aortic valve 412) and/or within the ventricle 416 of the patient's heart 410. Upon opening the distal containment section 438, the replacement heart valve implant 442 may shift toward and/or to an expanded deployed configuration. In some embodiments, the replacement heart valve implant 442 may be released from the distal containment section and/or the deployment device 440 prior to shifting to the expanded deployed configuration. In some instances, the replacement heart valve implant 442 may be released from the distal containment section and/or the deployment device 440 after shifting to the expanded deployed configuration.

Figure 16:
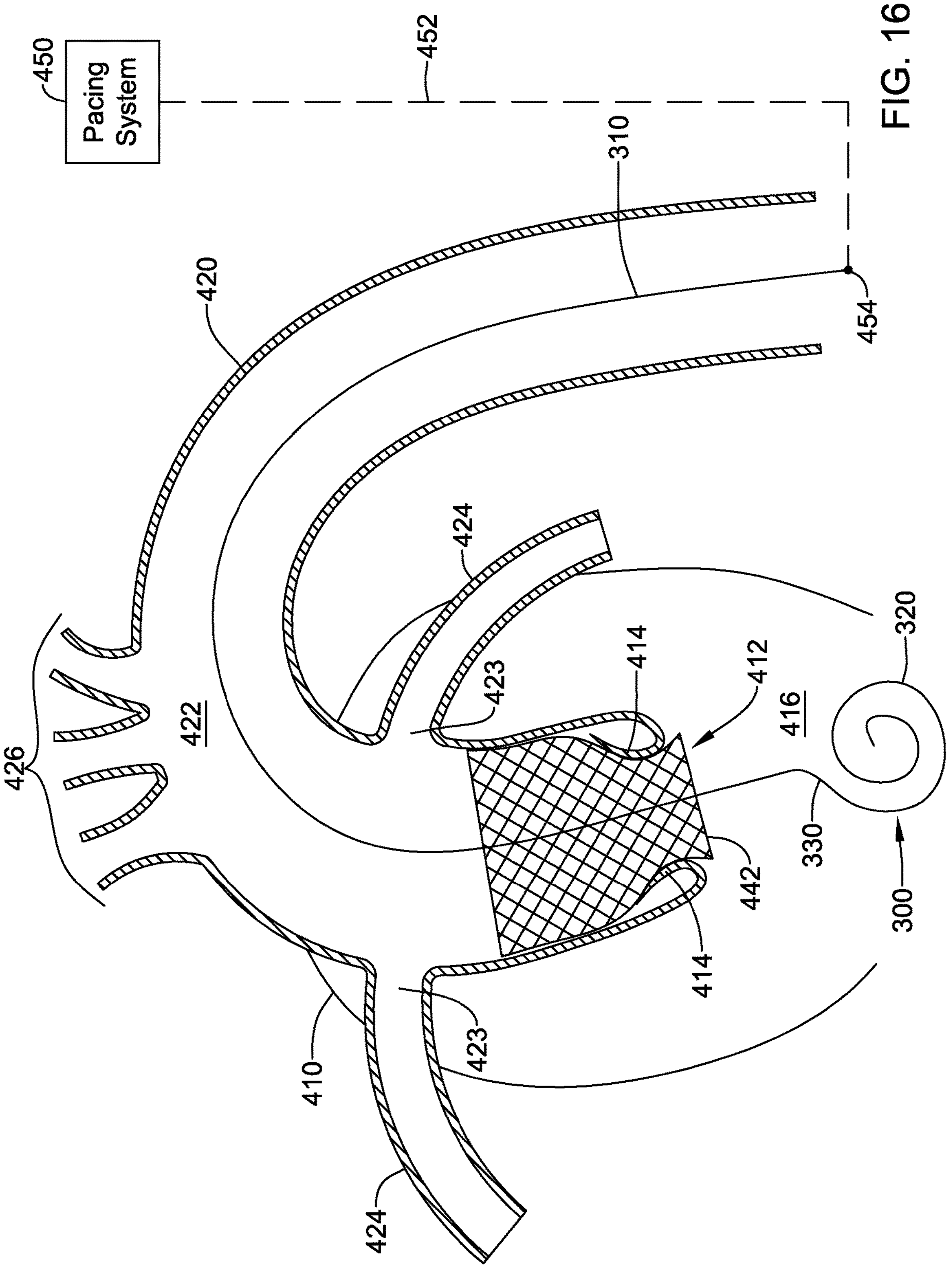

As can be seen in FIG. 15, the reverse curve portion 330 of the elongate shaft 310 of the guidewire 300 urges the distal portion of the proximal section 314 (not shown) of the elongate shaft 310 of the guidewire 300 toward a center of the native heart valve (e.g., the aortic valve 412) and/or away from the ostium of the native heart valve (e.g., the aortic valve 412). This positioning may prevent the distal portion 46 of the distal containment section 38 of the deployment device 440 from contacting the replacement heart valve implant 442 as the deployment device 440 is removed from the patient's heart 410, as seen in FIG. 16.

In some instances, the distal containment section 38 may be closed prior to removing the deployment device 40 from the patient's heart 10 and/or vasculature. In some instances, the deployment device 440 may be disposed within and/or may be retracted into a delivery catheter (not shown) prior to removal from the patient's heart 410 and/or vasculature. Other configurations are also contemplated.

In some instances, the catheter 430, the deployment device 440, the distal containment section 438, and/or elements thereof may include at least one radiopaque marker for visualization during delivery and/or navigation through the patient's vasculature. The at least one radiopaque marker may permit accurate placement under fluoroscopy of the distal end 432 of the catheter 430 and/or the distal containment section 438 of the deployment device 440 with respect to the native heart valve (e.g., the aortic valve 412), the ventricle 416, and/or the patient's heart 410.

In some instances, the physician or other professional implanting the replacement heart valve implant 442 may desire to use the guidewire 300 for delivering pacing pulses to the heart 410 during particular portions of the implantation process. In some instances, rapidly pacing the heart 410 during the implantation process may result in the heart 410 being less likely to displace the replacement heart valve implant 442 within the aortic valve 412. In some instances, as seen in FIGS. 14 through 16, a pacing system 450 may be utilized. The pacing system 450, which is shown schematically, may include a controller that determines when and how to pace, for example. The controller may also determine one or more pacing parameters for rapidly pacing the heart 410. An electrical cable 452 may extend from the pacing system 450, and may include a connector 454 that allows the electrical cable 452 to make an electrical connection with the guidewire 300. The connector 454 may take a variety of forms, depending on the construction of the proximal section 314 of the elongate shaft 310. The physician or other professional may utilize the pacing system 450 to pace during an appropriate step in implanting the replacement heart valve implant 442.

The materials that can be used for the devices described herein may include those commonly associated with medical devices. The devices described herein, or components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-clastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276R, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super-elastic nitinol in that the linear elastic and/or non-super-elastic nitinol does not display a substantial "superelastic plateau" or "flag region" in its stress/strain curve like super-elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super clastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super-elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-clastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, the devices described herein, or components thereof, may also be doped with, made of, or otherwise include a radiopaque material. Radiopaque materials are understood to be materials capable of producing a relatively bright image on a fluoroscopy screen or another imaging technique during a medical procedure. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into the devices described herein, or components thereof. For example, the devices described herein, or components thereof, may be made of a material that does not substantially distort the image and create substantial artifacts (e.g., gaps in the image). Certain ferromagnetic materials, for example, may not be suitable because they may create artifacts in an MRI image. The devices described herein, or components thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of the devices described herein in order to define a generally smooth outer surface. In other embodiments, however, such a sheath or covering may be absent. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the devices described herein may be sandblasted, beadblasted, sodium bicarbonate-blasted, electropolished, etc. In these as well as in some other embodiments, a coating, for example a lubricious, a hydrophilic, a protective, or other type of coating may be applied. Alternatively, a sheath may include a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

Portions of the devices described herein may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present disclosure.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A pacing tool adapted for use with a guidewire to allow the guidewire to be used for pacing, the guidewire having an electrically conductive proximal end, the pacing tool comprising:

a body defining an elongate cavity adapted to receive a guidewire, the elongate cavity including a proximal end;

a compressible electrical contact disposed at the proximal end of the elongate cavity, the compressible electrical contact adapted to shorten axially when a proximal end of the guidewire makes contact with the compressible electrical contact; and a cable electrically coupled with the compressible electrical contact, the cable adapted to be electrically coupled with a pacing system.

2. The pacing tool of claim 1, wherein the body comprises an electrically insulative material.

3. The pacing tool of claim 1, wherein the elongate cavity has an inner diameter that is adapted to frictionally engage an outer surface of the guidewire, thereby holding the guidewire in place within the elongate cavity with the proximal end of the guidewire electrically coupled with the compressible electrical contact.

4. The pacing tool of claim 1, wherein the elongate cavity has an inner diameter that is greater than an outer diameter of the guidewire, and wherein the pacing tool further comprises an actuatable element that is adapted to releasably engage a side of the guidewire when the guidewire is present within the elongate cavity in order to hold the guidewire in place within the elongate cavity.

5. The pacing tool of claim 4, wherein the actuatable element comprises a gripper adapted to releasably engage the side of the guidewire.

6. The pacing tool of claim 5, wherein the actuatable element further comprises a push button that is connected to the gripper via a compressible member.

7. The pacing tool of claim 6, wherein the compressible member comprises a spring.

8. The pacing tool of claim 1, wherein the compressible electrical contact comprises a pogo pin.

9. The pacing tool of claim 8, wherein the compressible electrical contact comprises:

a barrel element adapted to be secured to the proximal end of the elongate cavity;

a plunger element slidingly disposed within the barrel element and extending distally from the barrel element; and a spring disposed between the barrel element and the plunger element, the spring adapted to bias the plunger element distally relative to the barrel element but to allow the plunger element to move proximally relative to the barrel element in response to the guidewire being pushed against the compressible electrical contact.

10. The pacing tool of claim 9, wherein the plunger element is adapted to be held captive relative to the barrel element.

11. The pacing tool of claim 9, wherein the barrel element is adapted to be electrically coupled with the electrical cable.

12. A pacing tool adapted for use with a guidewire to allow the guidewire to be used for pacing, the guidewire having an electrically conductive proximal end, the pacing tool comprising:

a tool body defining:

an elongate cavity extending within the body, the elongate cavity adapted to accommodate a guidewire extending therein; and a channel orthogonal to the elongate cavity and coupled with the elongate cavity;

a guidewire holder slidingly disposed within the channel, the guidewire holder adapted to releasably engage a side of the guidewire when the guidewire is present within the elongate cavity in order to hold the guidewire in place within the elongate cavity; and a spring-loaded pin disposed at the proximal end of the elongate cavity, the spring-loaded pin adapted to shorten axially when a proximal end of the guidewire makes contact with the spring-loaded pin.

13. The pacing tool of claim 12, further comprising a cable electrically coupled with the spring-loaded pin, the cable adapted to be electrically coupled with a pacing system.

14. The pacing tool of claim 12, wherein the spring-loaded pin comprises:

a barrel element adapted to be secured to the proximal end of the elongate cavity;

a plunger element slidingly disposed within the barrel element and extending distally from the barrel element; and a spring disposed between the barrel element and the plunger element, the spring adapted to bias the plunger element distally relative to the barrel element but to allow the plunger element to move proximally relative to the barrel element in response to the guidewire being pushed against the spring-loaded pin.

15. The pacing tool of claim 14, wherein the plunger element is adapted to be held captive relative to the barrel element.

16. The pacing tool of claim 12, wherein the tool body comprises an electrically insulative material.

17. The pacing tool of claim 12, wherein the elongate cavity has a diameter that is greater than a diameter of the guidewire such that the guidewire is adapted to slide into the elongate cavity and is releasably held in place via the guidewire holder.

18. A pacing tool adapted for use with a guidewire to allow the guidewire to be used for pacing, the guidewire having an electrically conductive proximal end, the pacing tool comprising:

a tool body defining:

an elongate cavity extending within the body, the elongate cavity adapted to accommodate a guidewire extending therein; and a channel orthogonal to the elongate cavity and coupled with the elongate cavity;

a guidewire holder slidingly disposed within the channel, the guidewire holder comprising:

a gripper adapted to releasably engage a guidewire disposed within the elongate cavity;

a plunger adapted to be pushed in order to releasably engage the gripper; and a spring disposed between the gripper and the plunger;

a spring-loaded pin disposed at a terminal end of the elongate cavity; and a cable electrically coupled with the spring-loaded pin, the cable adapted to be electrically coupled with a pacing system.

19. The pacing tool of claim 18, wherein the spring-loaded pin comprises:

a barrel element adapted to be secured to the terminal end of the elongate cavity;

a plunger element slidingly disposed within the barrel element and extending distally from the barrel element; and a spring disposed between the barrel element and the plunger element, the spring adapted to bias the plunger element distally relative to the barrel element but to allow the plunger element to move proximally relative to the barrel element in response to the guidewire being pushed against the spring-loaded pin.

20. The pacing tool of claim 18, wherein the guidewire holder is adapted to translate within the channel.

* * * * *